United States Patent [19]

Wakatake

[11] Patent Number: 4,731,225
[45] Date of Patent: Mar. 15, 1988

[54] AUTOMATIC ANALYSIS APPARATUS

[75] Inventor: Koichi Wakatake, Koganei, Japan

[73] Assignee: Kabushiki Kaisha Nittec, Koganei, Japan

[21] Appl. No.: 901,383

[22] Filed: Aug. 28, 1986

[30] Foreign Application Priority Data

Jan. 31, 1986 [JP] Japan .................................. 61-18011
Apr. 19, 1986 [JP] Japan .............................. 61-59443[U]
Apr. 28, 1986 [JP] Japan .................................. 61-96951

[51] Int. Cl.$^4$ ............................................. G01N 35/04
[52] U.S. Cl. ........................................ 422/65; 422/67; 422/100; 436/47
[58] Field of Search ...................................... 422/63–67, 422/100, 102; 436/45, 47; 356/246

[56] References Cited

U.S. PATENT DOCUMENTS

| 3,526,480 | 9/1970 | Findl et al. | 422/66 |
| 4,263,256 | 4/1981 | Morle | 422/66 |
| 4,325,910 | 4/1982 | Jordan | 422/64 |
| 4,528,159 | 7/1985 | Liston | 422/64 |

OTHER PUBLICATIONS

The Paramax Analytical System–American Dade 7/1983.

Primary Examiner—Michael S. Marcus
Attorney, Agent, or Firm—Wenderoth, Lind & Ponack

[57] ABSTRACT

An automatic analysis apparatus of small size which meets the needs of regional hospitals or medium- or small-sized hospitals, and which is easy to handle and simple in construction. The apparatus employs reaction vessels of the disposable type so as to substantially completely prevent a problem of cross contamination while enabling a low running cost. The automatic analysis apparatus has a transfer path for transferring and guiding reaction vessels one by one in a linear manner, a reaction vessel transfer device for successively transferring the reaction vessels to a specimen discharging position, a reagent discharging position, an optical measuring position and a reaction vessel disposal position with respective predetermined timings, a specimen discharging device adapted to discharge a predetermined amount of a specimen to the reaction vessels at a specimen discharging position, a reagent discharging device adapted to discharge a predetermined amount of a reagent corresponding to a specimen being analyzed at a reagent discharging position, a stirring device for stirring a liquid in each of the reaction vessels, an optical measuring device for optically measuring the liquid in each reaction vessel, a disposal device adapted to discard, without cleaning, the reaction vessels the optical measurements on which are finished, and a central device for analyzing the data obtained by the optical measuring device.

7 Claims, 14 Drawing Figures

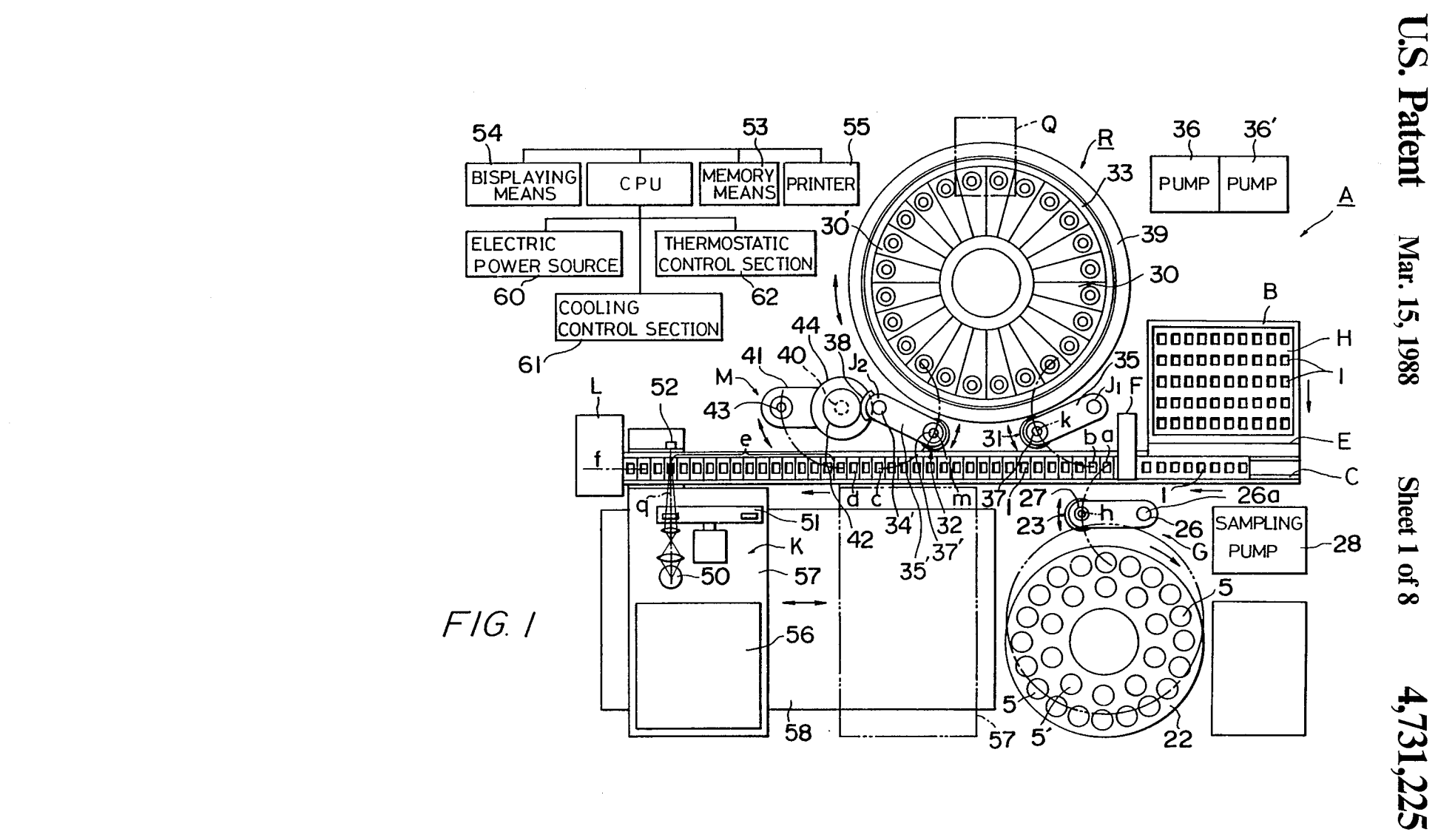

FIG. I

AUTOMATIC ANALYSIS APPARATUS

TECHNICAL FIELD

This invention relates to an automatic analysis apparatus for effecting a biochemical analysis or serological analysis of a biological body fluid such as blood, limph fluid, urine or the products resulting therefrom.

BACKGROUND ART

There have hitherto been developed a variety of automatic analysis apparatuses for analyzing a biological body fluid such as those as referred to above in order to obtain various useful information on the health of patients.

In these automatic analysis apparatuses developed in recent years, however, there is an increasing trend to deal with many test items by the use of a single automatic analysis apparatus in a short time and thus the appararus has been made more complicated in construction, larger in size, and higher in production costs and processing speed.

For this reason, many medium- or small-sized hospitals such as regional hospitals, practicing doctors or the like, not requiring so many test specimens and/or test items, have no strong need for installation of such large-sized and high-performance automatic analysis apparatus for themselves, and therefore, it is the general practice for such hospitals to forward test specimens such as blood to specialized test centers equipped with such large-sized and high-performance analysis apparatus for required testing such as blood analysis thereof for their own patients.

In these circumstances, whenever an emergency occurs in which urgent tests are required in the regional or medium- or small-sized hospitals having no automatic analysis apparatus, emergency test specimens have to be forwarded to the specialized test centers for biochemical or serological analysis thereof, and much time is thus needed until the results of such analysis are obtained. As a result, there often arises a problem in that one can not timely gain analytical data necessary for an operation on a patient and one has to defer the performance of such an operation, thus resulting in a waste of time and money.

Moreover, in many conventional automatic analysis apparatuses of the kind above described, reaction vessels and/or stirring rods are reused after being cleaned and hence provision has to made for cleaning devices for cleaning the reaction vessels and/or stirring rods each time a predetermined work is finished. This results in problems that the entire automatic analysis apparatus is further made greater in size, more complicated in construction and higher in production costs. In particular, in case of an immunological analysis, reuse of reaction vessels and/or stirring rods is liable to cause a problem of cross contamination due to insufficient or incomplete cleaning thereof.

In order to prevent such a cross contamination, it is effective to use reaction vessels and stirring rods of the disposable type, but in this case, the manufacturing and running costs thereof will increase to a material extent. In addition, it is necessary to manually set them in an automatic analysis apparatus in an appropriate manner and such manual steps are extremely inefficient and cumbersome.

Further, in automatic analysis apparatus in general, all kinds of reagents used will not be consumed uniformly and there will be a great difference in the consumed or reduced amount (i.e. the rate of reduction in volume) between reagents frequently used and those of infrequent use, as a consequence of which it is difficult for an inspector to visually check the volume of a reagent in each reagent bottle in order to ascertain that an appropriate volume of the reagent not less or greater than a suitable range is retained therein. Thus, reagent control is very difficult and troublesome.

DISCLOSURE OF THE INVENTION

In view of the above, a primary object of the present invention is to provide an automatic analysis apparatus of small size which meets the needs of regional hospitals or medium- or small-sized hospitals, and which is easy to handle and simple in construction.

Another object of the present invention is to provide an automatic analysis apparatus which employs reaction vessels of the disposable type so as to substantially completely prevent a problem of cross contamination while enabling a low running cost.

A further object of the present invention is to provide an automatic analysis apparatus which is most suited to a single analytical system as well as a single-multi analytical system so as to obtain data of analysis with a high level of precision.

A still further object of the present invention is to provide an automatic analysis apparatus in which the control of reagents is simple and easy.

In order to simultaneously achieve all the above-described objects, an automatic analysis apparatus of the present invention comprises a transfer path for transferring and guiding reaction vessels one by one in a linear manner, a reaction vessel transfer device for successively transferring the reaction vessels to a specimen discharging position, a reagent discharging position, an optical measuring position and a reaction vessel disposal position at respective predetermined timings, a specimen discharging device adapted to discharge a predetermined amount of a specimen to the reaction vessels at a specimen discharging position, a reagent discharging device adapted to discharge a predetermined amount of a reagent corresponding to a measuring item at a reagent discharging position, a stirring device for stirring a liquid in each of the reaction vessels, an optical measuring device for optically measuring the liquid in each reaction vessel, a disposal device adapted to discard, without cleaning, the reaction vessels the optical measurements of which are finished, and a control device for analyzing the data obtained by the optical measuring device.

BRIEF DESCRIPTION OF THE DRAWINGS

A few examples of an automatic analysis apparatus constructed in accordance with the present invention are illustrated in the accompanying drawings, in which:

FIG. 1 is a schematic plan view showing the general arrangement of an automatic analysis apparatus in accordance with the a first embodiment of the present invention;

BEST MODE FOR CARRYING OUT THE INVENTION

Figure 2:
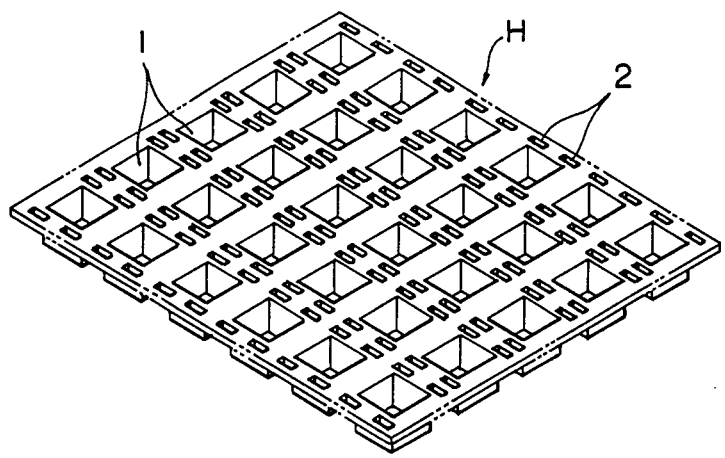
FIG. 2 is a perspective view showing an entire reaction vessel assembly.

FIGS. 1 through 9 show an automatic analysis apparatus in accordance with a first embodiment of the present invention.

The automatic analysis apparatus, generally designated by reference character A, comprises a reaction vessel assembly H in the form of a sheet having a predetermined number of reaction vessels 1 (fifty vessels in total including ten in the cross or lateral direction and five in the longitudinal direction per sheet in the illustrated embodiment) each provided with a liquid-receiving portion in the form of a bottomed polygonal cylinder, a stocker B for stocking a plurality of sheet-like reaction vessel assemblies H in a stacked manner, a reaction vessel transfer device C adapted to linearly transfer the respective reaction vessels 1 cut away from a reaction vessel assembly H to a specimen (serum) discharging position a, a first reagent discharging position b, a second reagent discharging position c, a stirring position d, an optical measuring position e, and a reaction vessel disposal position f, a first cutter device E for cutting a reaction vessel assembly H to separate vessels row by row (each having ten reaction vessels), a second cutter device F for cutting away, one by one, reaction vessels from a row already cut off assembly H by the first cutter E, a specimen discharging device G adapted to suck up a specimen from a sample vessel 5 and discharge it to reaction vessels 1 in a predetermined amount at the specimen discharging position a, a first and a second reagent discharging device $J_1$ and $J_2$ adapted to respectively suck up from a first and a second reagent vessel 30 and 30' a first and a second reagent corresponding to specific measuring items and discharge them to the reaction vessels 1 in respective predetermined amounts at the reagent discharging positions b and c, respectively, a stirring device M adapted to be operably connected with the second reagent discharging device $J_2$ for stirring reaction liquid in each reaction vessel 1 by means of air bubbles, an optical measuring device K, and a disposal device L for discarding the reaction vessels 1 the optical measurements of which are finished.

The reaction vessel assembly H is made from a light transmitting material such as plastics having flexibility and excellent chemical resistance, and is in the form of a sheet about 6 mm to 10 mm thick. The reaction vessel assembly H has a plurality (fifty in total in the illustrated example) of cup-shaped reaction vessels 1 arranged ten in the cross or lateral direction and five in the longitudinal direction. The reaction vessels are formed by injection moulding or vacuum moulding and are each of a rectangular shape in a plan view and of a concave or recessed form in cross section. Of course, the number of the reaction vessels 1 per sheet is not limited to that of the illustrated example.

The reaction vessels 1 may be contructed such that they have their top openings covered with a thin film which is adhered to the upper surfaces of the reaction vessels and which can be readily broken through by a sample pipette or a reagent pipette. In this manner, the interior of each of the reaction vessels 1 can be hermetically sealed by the thin film so that entry of foreign matters such as dust can be securely prevented.

Figure 3:
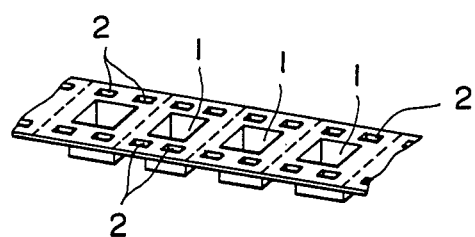
FIG. 3 is a perspective view showing a part of a row of reaction vessels cut away from the reaction vessel assembly.

As shown in FIG. 3, each row of the reaction vessels 1 is provided at the opposite widthwise sides thereof with engagement slots 2 which are disposed in the longitudinal direction at predetermined intervals for engagement with respective feeding claws 11b of the reaction vessel transfer device C.

Figure 4:
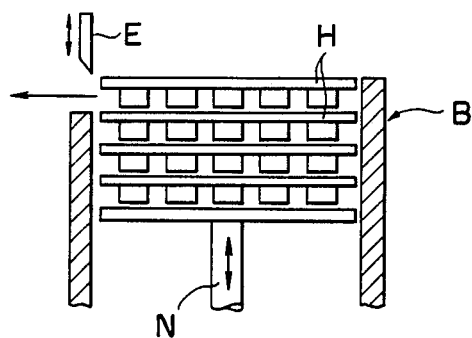
FIG. 4 is a cross sectional view showing a relationship between a stocker and reaction vessel assemblies received therein.

A plurality of sheet-like reaction vessel assemblies H as constructed in the above manner are received in the stocker B in a stacked state, as shown in FIG. 4, and the uppermost one of the reaction vessel assemblies H is transferred through an appropriate transfer device (not shown) to a feeding-side end (the righthand-side lower portion in FIG. 1) of the reaction vessel transfer device C and the vessels are cut away there row by row by means of the first cutter device E. One row of reaction vessel assembly H thus cut away is set at a transfer-starting end of the reaction vessel transfer device C.

In this connection, it is to be noted that the stocker B is constructed such that a predetermined number of sheet-like reaction vessel assemblies H can be stocked in a stacked manner, and the uppermost one of reaction vessel assemblies H set at the uppermost portion of the stocker B is intermittently transferred to the transfer-side end of the reaction vessel transfer device C pitch by pitch by means of an intermittent transfer device (not shown). After the uppermost reaction vessel assembly H has been entirely cut away and transferred row by row, the next one of reaction vessel assembly H is moved upward and set at the uppermost position by means of a lifting device N.

The above-mentioned one row of reaction vessels cut away from the assembly by the first cutter device E in turn has cut away one by one each vessel by means of the second cutter device F at a location at least one pitch before the specimen discharging position a. The reason for such cutting of the reaction vessel assembly H to cut away one vessel at a time by the second cutter device F is that if rows of cut-away reaction vessel assemblies H are transferred with a plurality of reaction vessels 1 continuously connected with each other, the last one of the reaction vessels 1 containing the last specimen to be analyzed has to be transferred to the disposal position f and discarded there together with the remaining unused reaction vessels for completion of the analysis operation. Thus, to cut the reaction vessels of the same row away from each other is economical and makes it easy to handle the reaction vessels for the purpose of disposal.

In this connection, it is to be noted that though not shown, the first and second cutters devices E and F each having a holding plate, a cutting blade and a feeder, similar to the construction of a known conventional cutter device.

The respective reaction vessels 1 cut away one by one by the second cutter device F are successively transferred by the reaction vessel transfer device C along the linear transfer path thereof in a direction toward the optical measuring position e.

Figure 5:
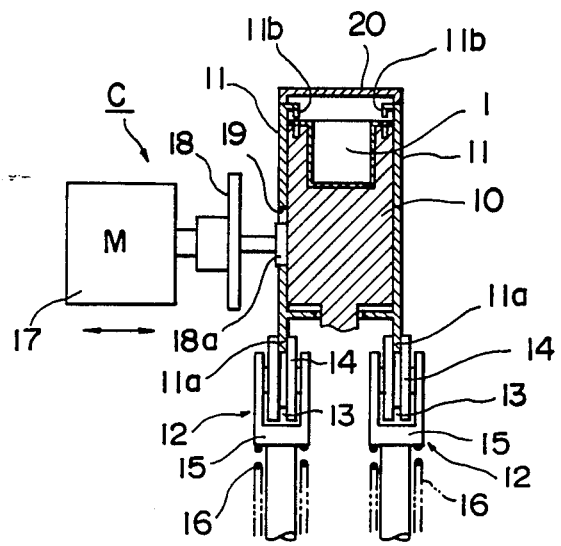
FIG. 5 is a cross sectional view showing the construction of a reaction vessel transfer device with a part thereof omitted.

As shown in FIG. 5, the transfer path of the reaction vessel transfer device C is in the form of a U-shaped cross section and disposed on the upper surface of a heating block 10 which is fixed to the bottom of the transfer path against any movement relative thereto. A pair of side walls 11 are disposed on and connected with the opposite sides of the heating block 10 in a manner such that they are movable in concert relative to the heating block 10 in the lateral and vertical directions.

The side walls 11 thus constructed are supported at their lower ends 11a by elastic support members 12, respectively. The elastic support members 12 each comprise a roller 14 having on its upper portion a groove 13 into which the lower end 11a of the corresponding side wall 11 engages, a holder 15 rotatably supporting the roller 14, and a spring 16 for biasing the holder 15 in the upward direction in the normal operating condition.

Four pairs of the elastic support members 12 as constructed above are disposed at four corners of the above-mentioned transfer path so as to support the side walls 11 for movements in the lateral and vertical directions. The side walls 11 thus supported by the elastic support members 12 are driven to move in the lateral and vertical directions by means of a motor 17.

Specifically, the motor 17 has a rotary shaft on the tip end of which is fixedly mounted a cam 18 having a circular eccentric member 18a. The eccentric member 18a is engaged with a square-shaped engagement notch 19 formed in one of the side walls 11 so that both of the side walls 11 are driven to move in the lateral and vertical directions in accordance with the rotation of the eccentric member 18a. As a result, the feeding claws 11b formed on the upper ends of the side walls 11 are brought into engagement with the engagement slots 2 in the respective reaction vessels 1 so as to feed them one pitch at a time toward the optical measuring position e.

In this regard, it should be noted that though the side walls 11 are biased upward under the action of the elastic support members 12 as referred to above, the upward movement of the side walls 11 caused by the motor 17 is restricted by a closure of lid member 20 to be described in detail later.

A plurality of pairs of such cams 18 and motors 17 thus constructed are disposed along the longitudinal direction of the trasfer path at predetermined intervals (one pitch).

Now, a description will be given of the way the reaction vessels 1 are transferred by the reaction vessel transfer device C as constructed in the above manner.

Figure 6B:
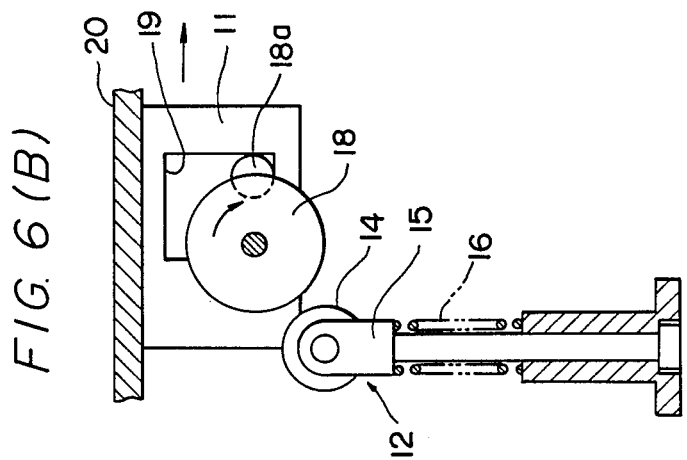
FIG. 6A through 6D are explanatory views respectively showing different operating states in which a reaction vessel is successively transferred by means of the reaction vessel transfer device.
Figure 6A:
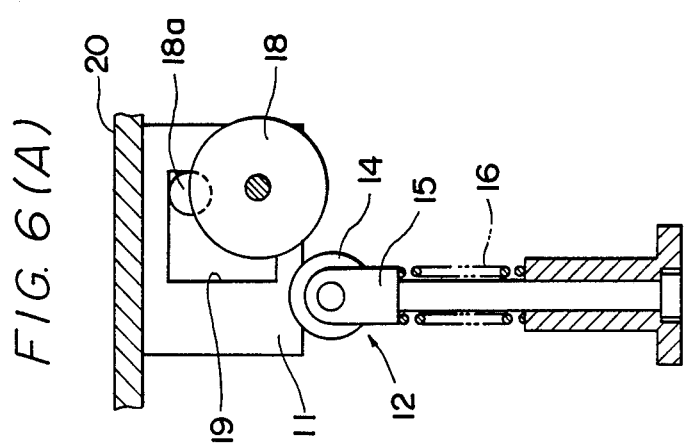

When reaction vessels 1, being cut one by one by means of the second cutter device F, are set on the transfer path, as illustrated in FIG. 6A, the circular eccentric member 18a of the cam 18 is positioned at right angles relative to the horizontal and thus in contact with the right upper portion of the inner peripheral surface of an engagement notch 19 formed in the one side wall 11. In this case, the respective feeding claws 11b on the upper ends of the side walls 11 are out of engagement with the engagement slots 2 in the reaction vessels 1.

As the cam 18 is turned through an angle of 90 degrees from this position in the clockwise direction in FIG. 6 toward a position in which the angle of the eccentric member 18a relative to the horizontal is 180 degrees, the side walls 11 are pushed down by the eccentric member 18a so that the respective feeding claws 11b on the upper ends of the walls 11 are brought into engagement with the engagement slots 2 in the reaction vessels 1. In this case, the downward movement of the side walls 11 is stopped by the eccentric member 18a which comes in contact with the right-hand lower portion of the inner peripheral surface of the engagement notch 19, as shown in FIG. 6B.

Figure 6D:
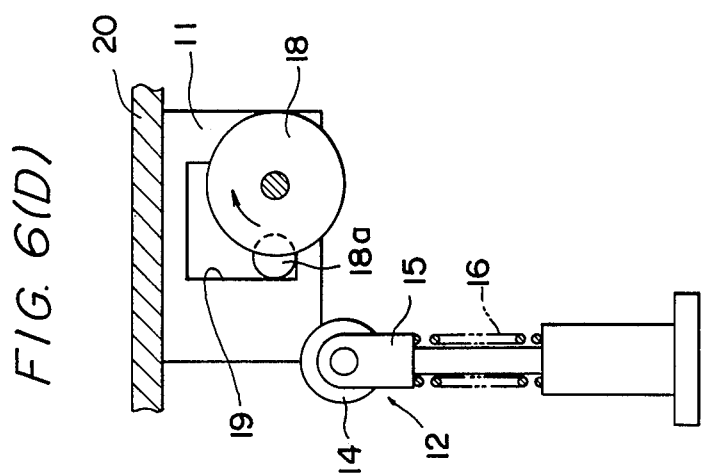
Figure 6C:
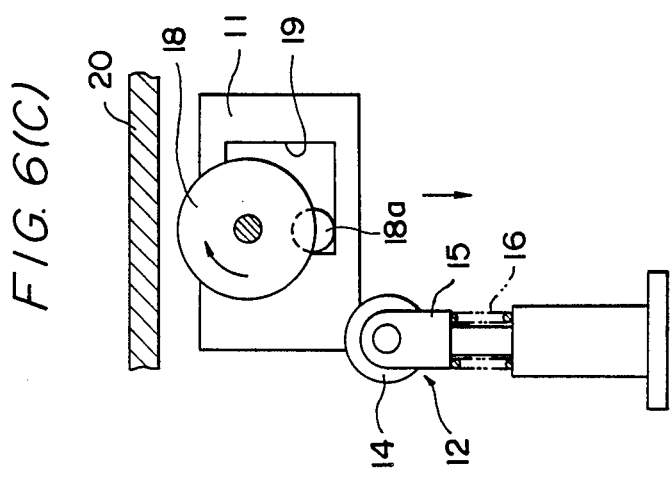
Figure 7:
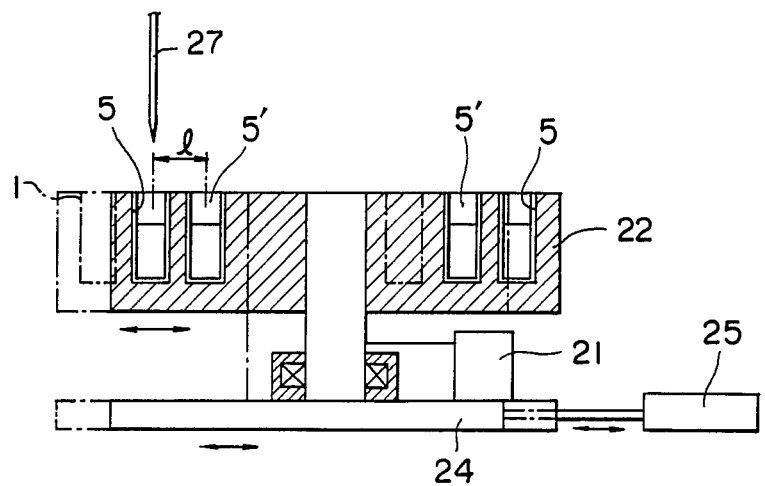
FIG. 7 is a cross sectional view schematically showing the construction of a sample holder transfer device.

Thereafter, at the time when the eccentric member 18a is further turned through 90 degrees in the clockwise direction to a position of 270 degrees relative to the horizontal, as shown in FIG. 6C, the side walls 11 are urged by the eccentric member 18a against the biasing force of the spring 16 to advance one pitch in the leftward direction in FIG. 6C, thereby transferring the reaction vessels 1 in the leftward direction.

Subsequently, as the eccentric member 18a is further turned clockwise to a position of zero degrees relative to the horizontal, as shown in FIG. 6D, the side walls 11 are forced to move upward under the bias of the spring 16, thus returning to the original position. Thereafter the cam 18 is turned to a position shown in FIG. 6A and the side walls 11 are thereby forced to move upward to a position in which they come into abutting engagement with the closure member 20 whereby the feeding claws 11b on the upper ends of the side walls 11 are placed out of engagement with the engagement slots 2 in the reaction vessels 1 with the result that the reaction vessels 1 alone are advanced forward one pitch.

The reaction vessels 1 thus advanced one pitch are further forwarded pitch by pitch in the same manner as described above by means of a motor and a cam (not shown) which are disposed at the next transfer position and which are constructed in the same manner as referred to above.

The closure or lid member 20 has throughapertures (not shown) through which the sample pipette 27, the reagent pipettes 31 and 32, and the stirring rod 43 are inserted into the interior of each reaction vessel 1.

In the heating block 10 is embedded a heating member such as an electric resistance wire like a nichrome wire so that the specimens in the reaction vessels 1, being transferred along the transfer path, are heated to a temperature of about 37° C. during transfer thereof.

The specimen discharging device G comprises a sample holder 22 adapted to be rotated in the clockwise direction in FIG. 1 by means of a drive means 21, and a sampling pipette 23 for sucking up a predetermined amount of a specimen in a sample vessel 5 held by the sample holder 22 at a sample sucking position g. The sample holder 22 holds, around its outer periphery, a predetermined number of first sample vessels 5 in a loop-like pattern and a predetermined number of second sample vessels 5' likewise arranged in a loop-like pattern around the inner periphery of the loop-like arranged first sample vessels 5. The first sample vessels 5 store ordinary specimens whereas the second vessels 5' store ordinary specimens or measuring specimens and urgent specimens (test pieces).

The sample holder 22 acts to intermittently transfer the sample vessels 5 or 5' to the sample sucking position g through the intermediary of a driving device. As pictured in FIG. 7, the sample holder 22 is pivotally supported on a support member 24 which is slidable linearly in the upward direction in FIG. 1, the support member 24 being driven to slide by virtue of a sliding means 25 such as an actuator upon sucking up of the specimens into the second reaction vessels 5'. In this case, the sliding stroke of the support member 24 is determined such that it corresponds to an interaxis distance between the first and second sample vessels 5 and 5', i.e. a distance between the major axes of the sample vessels 5 and 5'.

When the sample vessels 5 or 5' are transferred to the predetermined sample sucking position g in the above manner, a predetermined amount of a specimen in each of the sample vessels 5 or 5' is sucked by a sampling pipette 23 and discharged into the respective reaction vessels 1.

As seen from FIG. 1, the sampling pipette 23 is similar in construction to a known one and comprises an arm 26 pivotally supported at its one end on a shaft 26a, a pipette 27 mounted on the other end of the arm 26, a sampling pump 28 communicatively connected with the pipette 27 and adapted to suck up a predetermined amount of a specimen in the respective one of the sample vessels 5 or 5' and discharge it to the reaction vessels 1, and a drive means (not shown) adapted to rotate the arm 26 from the sample sucking position g to the specimen discharging position a and thence to the cleaning position h at predetermined times and move it in the vertical direction at the respective positions in a controlled manner.

Each of the specimens in the sample vessels 5 and 5' is a predetermined amount of liquid which has been sucked up by the sampling pipette 23 in the following manner. The suction system including the pipette 27 and the sampling pump 28 is first filled with water, and the specimen and water, being separated from each other by air interposed therebetween, are sucked up and measured by the pipette 27, and only the specimen thus sucked up and measured is then discharged therefrom. Thereafter, cleaning water is supplied to the pipette 27 from an appropriate cleaning water supply means to flow down through the interior of the pipette 27 for cleaning thereof. At the time of this cleaning, the pipette 27 is, of course, set at the pipette cleaning position h and the residual specimen adhered on the interior surface of the pipette 27 is washed away at this position.

The reagent device R comprises first reagent bottles 30 and second reagent bottles 30' respectively storing different reagents corresponding to specific measuring items, a bottle transfer device (not shown) for turning a table 33 on which the reagent bottles 30 and 30' are rested so as to transfer the bottles 30 and 30' to a first reagent sucking position i or a second reagent sucking position j, respectively, a first reagent pipette device 31 for sucking up a predetermined amount of a first reagent corresponding to a first measuring item from a first reagent bottle 30 at the first reagent sucking position i, and a second reagent pipette device 32 for sucking up a predetermined amount of a second reagent corresponding to a second measuring item from a second reagent bottle 30' at the second reagent sucking position j. In this connection, it is to be noted that the first and second reagent bottles 30 and 30' rested on the table 33 are preset at respective predetermined positions which are respectively memorized by a control device CPU to be described in detail later.

In FIG. 1, reference numeral 39 designates a reagent cooling chamber for cooling the reagents in the reagent bottles 30 and 30' to temperatures in a range from 10° C. to 12° C.

When the reagent bottles 30 and 30' corresponding to specific measuring items come to the respective predetermined reagent sucking positions i and j, respectively, the respective reagents in the reagent bottles 30 and 30' are respectively sucked up by the first and second reagent pipette devices 31 and 32 in respective predetermined amounts and discharged to the reaction vessels 1.

The first and second reagent pipette devices 31, 32 are constructed in a manner similar to known pipetting devices and each comprise an arm 35 or 35' pivotally supported at its one end on a shaft 34 or 34', a pipette 37 or 37' mounted on the other end of the arm 35 or 35', a pump 36 or 36' communicatively connected with the pipette 37 or 37' and adapted to suck up a predetermined amount of a reagent in the respective one of the reagent bottles 30 or 30' and discharge it to the reaction vessels 1, and a drive means (not shown) adapted to rotate the arm 35 or 35' from the reagent sucking position i or j to a reagent discharging position b or c and thence to a cleaning position k or m at predetermined times and move it in the vertical direction at the respective positions in a controlled manner.

Each of the reagents in the reagent bottlers 30 and 30' is sucked up and measured in a predetermined amount by the reagent pipette device 31 or 32 in the following manner. The suction systems each including the pipette 37 or 37' and the pump 36 or 36' are first filled with water, and the reagent and water, being separated from each other by air interposed therebetween, are sucked up and measured by the pipette 37 or 37' and only the reagent thus sucked up and measured is then discharged therefrom. Thereafter, cleaning water is supplied to the pipette 37 or 37' from an appropriate cleaning water supply means to flow down through the interior of the pipette 37 or 37' for cleaning thereof. Upon this cleaning, the pipette 37 or 37' is, of course, set at the pipette cleaning position k or m and the residual reagent adhered on the interior surface of the pipette 37 or 37' is washed away at this position.

Figure 8:
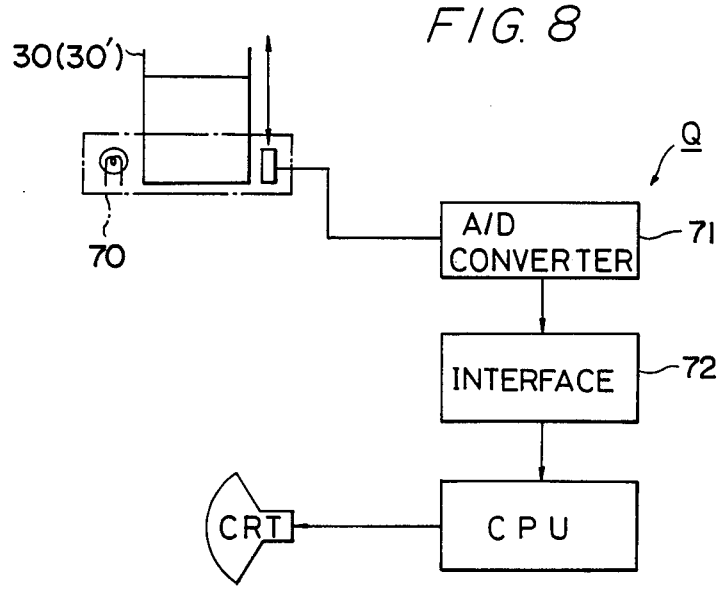
FIG. 8 is a block diagram showing the construction of a display device for displaying the liquid volume and the number of samples.
Figure 9:
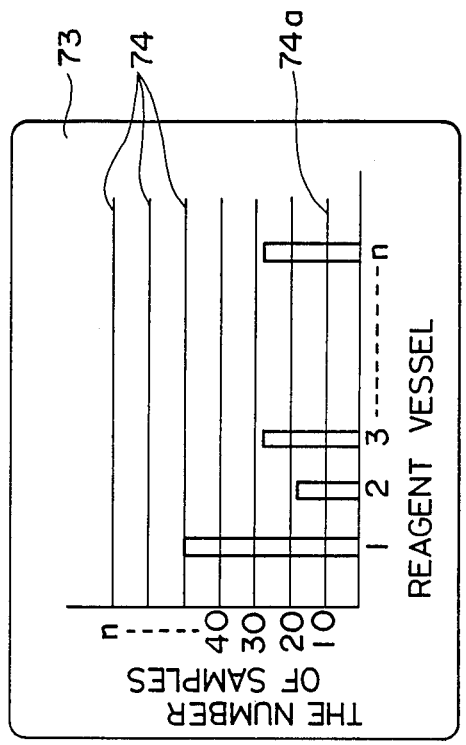
FIG. 9 is an explanatory view showing a display mode representative of the residual liquid volumes in respective reagent vessels and the number of samples.

The reagent device R is provided with a liquid-volume and sample-number indicating means Q. As illustrated in FIG. 8, the liquid-volume and sample-number indicating means Q comprises a liquid-volume measuring device 70 for optically measuring the volume of a liquid or reagent contained in each of the reagent bottles 30 and 30', an A/D converter 71 adapted to convert a liquid level signal measured by the liquid-volume measuring device 70 into a digital signal, an interface 72, the above-mentioned control device CPU, an indicator device 73 such as a cathode-ray tube adapted to be operated by a command signal from the control device CPU to indicate the remaining volumes of liquids or reagents contained in the respective reagent bottles 30 and 30', for example, with a bar graph representation as illustrated in FIG. 9. The control device CPU is constructed such that sample number lines 74 are indicated on a screen of the indicator device 73 in a horizontal manner at predetermined intervals.

The liquid-volume and sample-number indicating means Q may be a known liquid contact type employing electrodes or a liquid non-contact type employing optical means, and constructed such that the remaining volume of a liquid in each of the reagent bottles 30 and 30' is calculated by a known operation process on the basis of a liquid level measured by the electrodes or the optical means.

The remaining volume of the liquid in each of the reagent bottles measured by the liquid-volume measuring device 70 is processed such that it is represented as a bar graph on the cathode-ray tube 73 by the control device CPU. In this case, the volumes of the reagents in the respective reagent bottles 30 and 30' consumed per test differ in terms of measuring items, and the sample number lines 74 are represented as horizontal lines at predetermined intervals. Therefore, the control device UPU operates to correct the remaining liquid volumes in the respective reagent bottles 30 and 30' in a manner such that the remaining volumes of the reagents necessary for test specimens is uniformly indicated at equal intervals.

In FIG. 9, reference numeral 74a designates a warning indication line. The liquid-volume and sample-number indicating means Q may be constructed such that if the upper end of at least one bar is below this line 74a, a warning will be given by operating a buzzer or changing the color of the bar in question so that the reagent bottle short of a reagent can be replenished.

With the liquid-volume and sample-number indicating means Q as constructed in the above manner, an operator can ascertain at a glance the amounts of reagents in the respective reagent bottles 30 and 30' and the possible number of samples still able to be treated. As a result, the operator can replenish the reagents by taking into account the expected number of tests to be conducted in the day so that the control of reagents in the automatic analysis apparatus A becomes easy and the operation efficiency of the automatic analysis apparatus A is markedly improved.

The stirring device M comprises an arm 41 rotatable around a shaft 40, a spur gear wheel 42 fixedly mounted on the arm 41, a tube 43 for feeding air into a specimen in a reaction vessel 1, a cutter (not shown) adapted to cut away the portion of the tube 43 which has once been inserted into and contacted the specimen in the reaction vessel 1, a feeding means (not shown) for feeding a predetermined length of the tube 43 step by step, and a tube stocker 44 adapted to stock the tube 43 in a wound state. The spur gear wheel 42 is in meshing engagement with the gear 38 mounted on the arm 35' of the above-mentioned second reagent pipette device 32. Accordingly, when the arm 35' is set at the cleaning position m, as illustrated in FIG. 1, the arm 41 of the stirring device 41 is in a waiting state. Subsequently, upon rotation of the arm 35' toward the second reagent sucking position j in the counterclockwise direction in FIG. 1, the engagement between the spur gear wheel 42 fixed to the arm 41 and the gear 38 mounted on the arm 35' is released so that the arm 41 is held stationary at the waiting position.

Thereafter, when the pipette 32 sucks up a predetermined amount of the second reagent and then the arm 35' is caused to rotate in the clockwise direction in FIG. 1 toward a reaction vessel 1, the gear 38 on the arm 35' is again placed in meshing engagement with the spur gear 42 on the arm 41 whereby the arm 41 is forced to rotate in the counterclockwise direction in FIG. 1 toward the reaction vessel 1 thereby to place the tip end of the tube 43 just above the reaction vessel 1.

The arm 35' is then lowered to an appropriate level and discharging operation of the second reagent is started. With the descending movement of the arm 35', the arm 41 is pushed down by the arm 35' so that the tip end of the tube 43 is inserted into the specimen in the reaction vessel 1 and supplies air into the specimen for stirring thereof by air bubbles.

When the reagent discharging operation of the pipette 32 has been finished in this manner, the arm 35' is raised and the arm 41 is also forced to move upward under the bias of a spring (not shown). Thereafter, as the arm 41 is caused to rotate in the counterclockwise direction in FIG. 1 toward the above-mentioned cleaning position m, the arm 41 is rotated clockwise in FIG. 1, returning to the initial or original position. At this time, utilizing the rotational force of the arm 41, a cutter (not shown) is operated to cut away the tube 43 in an appropriate manner. The purpose of such a cutting of the tube 43 is to cut away that portion of the tube 43 which has once contacted a specimen in a reaction vessel 1, thus avoiding any error in measurements resulting from a contamination between different specimens.

The optical measuring device K, which constitutes a detecting section or an observation point, comprises a light source 50, a filtering means 51 adapted to selectively permit the passage therethrough of a measuring light beam which is emitted from the light source 50 and which has a specific wavelength corresponding to a measured item, a photosensitive element 52 adapted to receive the measuring light beam of the specific wavelength which has been selected by the filtering means 51 and which has passed through a reaction vessel 1, the above-mentioned control device CPU adapted to convert the intensity of the light beam received by the photoelectric element 52 into a voltage and then process it in an appropriate manner to provide analytical data, a memory means 53 for memorizing the analytical data of the control device CPU, a displaying means 54, a printer 55, a stabilizing power source and detecting circuit 56, a housing unit 57 for accommodating therein the light source 50, the filtering means 51, the photoelectric element 52 and the stabilizing power source and detecting circuit 56, and a detector transfer means 58 for slidably reciprocating the housing unit 57 along the reaction vessel transfer path. Of course, the light source 50 and the photoelectric element 52 are disposed across the reaction vessel transfer path in a face-to-face relation with each other.

The optical measuring device K is arranged such that the reaction vessels 1 go across a light path q of a light beam emitted from the light source 50 so that the specimens in the reaction vessels 1 are measured in terms of specific color upon passage thereof across the light beam.

The detector transfer means 58 is constituted by a known linear-slide guiding mechanism such as, for example, a ball screw (a recirculating ball bearing), a combination of a slide guide and a wire, and the like. The detector transfer means 58 is slidably guided along the reaction vessel transfer path in a manner such that the light beam from the light source 50 can pass through the respective interiors of a plurality of reaction vessels 1, for example, seventeen vessels at maximum. Specifically, the arrangement is such that the light beam can pass through the respective interiors of seventeen vessels 1 in the direction from the second reagent discharging position c toward the reaction vessel disposal position f. This is because the specimen blanks can be measured before the second reagent is discharged to the reaction vessels 1 at the second reagent discharging position c. Accordingly, in case where there is no need for measuring such specimen blanks, it may be arranged such that the light beam from the light source 50 starts to pass through the reaction vessels 1 from the stirring position d.

For this reason, the optical measuring device K can measure all of the seventeen reaction vessels 1 starting from the second reagent discharging position c, for example, every 20 seconds for a duration of 5 minutes in a continuous manner so as to obtain a reaction time course of the respective reaction vessels 1.

The disposal device L is arranged at the terminal end of the reaction vessel transfer path and is in the form of a box having its bottom closed but its top open. All the reaction vessels 1, on which all the measuring operations have been completed, will be thrown into the disposal device L from its top opening at the disposal position f.

The control device CPU functions to control the operation of the automatic analysis apparatus A and conducts the operation of measuring signals and judgement of the results obtained.

In FIG. 1, reference numerals 60, 61 and 62 designate an electric power source, a cooling control section and a thermostatic control section, respectively. The specimens in the reaction vessels transferred along the transfer path are heated to a temperature of 37° C. under the action of the thermostatic control section 62, as referred to in the foregoing.

PREFERRED OPERATION OF THE INVENTION

Now, a description will be given of an automatic analysis performed by the automatic analysis apparatus in accordance with the above-described embodiment.

First, when the power source 60 and a start switch (not shown) are turned on, a reaction vessel assembly H in the form of a sheet is pushed out from the stocker B toward the transfer path and reaction vessels are cut away row by row (each having ten reaction vessels) by the first cutter device E so as to be set on the transfer path.

One row of the reaction vessels 1 thus set on the transfer path is intermittently fed a one vessel length step by step in the leftward direction in FIG. 1 under the action of the reaction vessel transfer device C, and then individual vessels are cut away one by one by means of the second cutter device F at a location at least one pitch before the specimen discharging position a.

The individual reaction vessels 1 cut away one by one in this manner are transferred to the specimen discharging position a. On the other hand, in response to this transfer, the specimen discharging device G sucks up a predetermined amount of a specimen contained in one of the sample vessels 5, 5' set at the specimen sucking position g, and is then rotated to the specimen discharging position a where the respective specimens sucked up by the specimen discharging device C are discharged to the respective reaction vessels 1.

Thereafter, the reaction vessel transfer device C intermittently forwards pitch by pitch the reaction vessels 1 thus filled with the specimens toward the first reagent discharging position b.

When the reaction vessels 1 arrive at the first reagent discharging position b, the reagent table 33 is controlled to turn in synchronism with this arrival, and a first reagent bottle 30 containing a reagent corresponding to a specific specimen is set at the reagent sucking position i where a predetermined amount of the first reagent in the first reagent bottle 30 is sucked up by the first reagent pipette device 31 and discharged therefrom amount into the respective reaction vessels 1 which have reached the first reagent discharging position b.

Thereafter, the reaction vessels 1 are fed at a predetermined pitch (i.e. a length of sixteen vessels in the illustrated embodiment) toward the second reagent discharging position c. In response to this, the reagent table 33 is controlled to turn so that a second reagent bottle 30' containing a second reagent corresponding to a specific specimen is transferred to the second reagent sucking position j where a predetermined amount of the second reagent is sucked up by the second reagent pipette 32 and discharged therefrom into the reaction vessels 1 at the second reagent discharging position c.

At the position d spaced one pitch away from the second reagent discharge position c in the forward direction, the specimen and the first and second reagents in each reaction vessel 1 are stirred by means of air bubbles.

Subsequently, the reaction vessels 1 held by the heating block 10 are advanced by the transfer device C toward the optical measuring position e where an optical measurement on the reaction vessels 1 is effected by means of light of a specific wavelength corresponding to the specimen being tested, and the course of the reaction with the passage of time in every reaction vessel 1 is measured by successive measurements of light passed through the respective reaction vessels during the sliding movement of the housing unit 57 from the dotted-line position toward the full-line position in FIG. 1. In this connection, it should be noted that the principle of the specific color measurement by means of the filtering device 51 in which a specific color measurement is made by change-over of filters is well known and hence a detailed explanation thereof is omitted.

The data of the analysis thus obtained by the optical measurement is input to and processed by the control device CPU and displayed by the display means 54 or printed out by the printer 55 as necessary.

After finishing of the optical measurement, the reaction vessels 1 are transferred to the reaction vessel disposal position f and thrown into the disposal device L.

Although in the above-described embodiment, the reaction vessel transfer means comprises an eccentric cam mechanism, it is not limited to this. For example, a gear transmission or an endless belting may be utilized with similar operational effects. Likewise, the optical measuring device is not limited to the one employed in the above embodiment but may be of a diffraction grating type. Also, the cutter device may be disposed just before the reaction vessel disposal position.

DESCRIPTION OF ANOTHER PREFERRED EMBODIMENT

Figure 10:
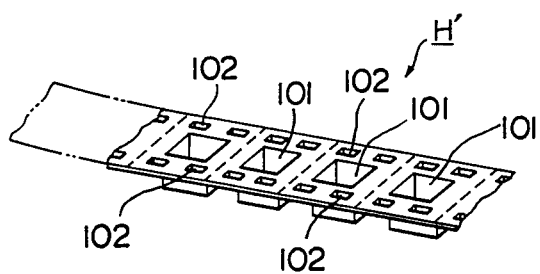
FIG. 10 is a perspective view showing another reaction vessel assembly applicable to an automatic analysis apparatus in accordance with a second embodiment of the present invention.
Figure 11:
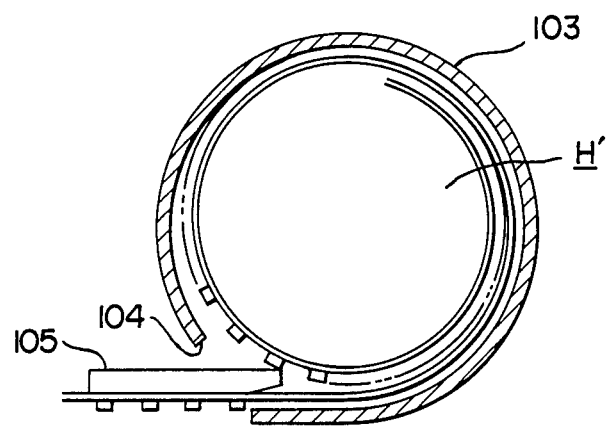
FIG. 11 is a cross sectional view showing a relationship between a stocker and a reaction vessel assembly received therein.

FIGS. 10 and 11 illustrate another embodiment of the reaction vessel assembly H' in accordance with the present invention.

The reaction vessel assembly H' illustrated is formed of a light transmitting material such as plastics having flexibility and excellent chemical resistance and takes the form of an elongated band or belt having a thickness of about 6 mm to 10 mm. The reaction vessel assembly H' has a plurality of reaction vessels 101 formed therealong the longitudinal direction at predetermined intervals and continuously connected with each other, each of the reaction vessels 101 being of a cup-shaped configuration having a rectangular form in plan view. Of course, it is preferable that the reaction vessel assembly 101 be made by injection moulding or vacuum moulding.

The reaction vessel assembly H' has an upper thin plate-like portion provided at its opposite widthwise sides with a multitude of perforations or engagement slots 102 which are engageable with the feeding claws 11b of the aforementioned reaction vessel transfer device C, the perforations 102 being formed by punching, press working or the like at predetermined intervals in the longitudinal direction. In FIG. 11, reference numeral 105 designates a presser plate for straightening the unwound portion of the wound band- or belt-like reaction vessel assembly H' as described later.

As clearly shown in FIG. 11, the reaction vessel assembly H' as constructed in this manner is stored in a stocker 103 in a wound state and in use, the tip end portion of the reaction vessel assembly H' is successively pulled out vessel by vessel from an opening 104 in the stocker 103 and, as referred to before, and reaction vessels are cut off one by one by means of the second cutter device F at a location before the transfer-starting end of the reaction vessel transfer device C. In this case, the stocker 103 may be a cassette type one having therein a pre-wound reaction vessel assembly H' or a wound reaction vessel assembly H' may be manually loaded into the stocker 103.

The transfer process of the reaction vessel assembly H' thus constructed is similar to that of the aforesaid first embodiment and therefore a detailed description thereof is omitted.

As will be understood from the foregoing description, according to the present invention, it is possible to make the entire apparatus compact and simple so that an automatic analysis apparatus having less trouble can be produced at low cost. Thus, there will be provided an automatic analysis apparatus of a single or a single-multi type which is most suited to the requirements of medium- or small-sized hospitals.

Further, the present invention employs reaction vessels of the disposable type, that is reaction vessels are not cleaned for reuse but are discarded once they are used for measurement. For this reason, the problem of cross contamination between the reaction vessels can be substantially eliminated or greatly reduced, and hence the automatic analysis apparatus of the invention is highly suited for immunological analysis. In addition, there is no need for the provision of any cleaning device so that the apparatus is simple in construction and easy to handle, thus enabling a substantial reduction in the overall dimension thereof.

What is claimed is:

1. An apparatus for carrying out automatic analysis of a specimen carried in a transparent reaction vessel, said apparatus comprising:
    a transfer path along which reaction vessels are transferred one by one in a linear manner, said path having therealong and in the recited order a specimen discharging position, at least one reagent discharging position, a series of successive optical measuring positions, and a reaction vessel disposal position;
    a reaction vessel transfer device for successively transferring reaction vessels along said transfer path for bringing successive reaction vessels to each position one at a time;
    a specimen discharging device at said specimen discharging position for discharging a predetermined amount of a specimen to be analyzed into a reaction vessel at said specimen discharging position;
    at least one reagent discharging device at said at least one reagent discharge position for discharging a predetermined amount of a reagent at said reagent discharging position;
    a stirring device along said transfer path between said at least one reagent discharge position and the first of said series of optical measuring positions for supplying gas for stirring the liquid in each reaction vessel;
    an optical measuring device for passing a beam of light through the liquid in each rotation vessel, said optical measuring device including a light source and a photoelectric element disposed on opposite sides of said transfer path in face-to-face opposed relation to each other, and a filtering device in the path of the light beam from said light source for permitting the passage of light having a specific wavelength corresponding to the specimen being analyzed, said optical measuring device being movable along said transfer path past said succession of optical measuring positions in the direction of movement of reaction vessels along said transfer path for directing the beam of light through each reaction vessel at said optical measuring positions;
    an optical measuring device transfer means connected to said optical measuring device for moving said optical measuring device along said transfer path;
    a control device connected to said optical measuring device and comprising means for analyzing the data obtained by said optical measuring device; and
    a disposal device at said reaction vessel disposal position for discarding, without cleaning, each reaction vessel for which the optical measurements are finished.

2. An apparatus as claimed in claim 1 further comprising means for feeding reaction vessels which are in the form of a sheet made of a light transmitting synthetic resin having excellent chemical resistance and in which sheet reaction vessels are arranged in rows transversely of the sheet with slots along the opposite sides of the rows, said feeding means comprising a storage means in which the sheets are stored in a stack one on the other, means for feeding the top sheet out of said storage means, means for cutting the sheet being fed to separate rows of reaction vessels from the remainder of the sheet and place the cut off row onto said reaction vessel transfer device, and further means for cutting the rows of reaction vessels for separating reaction vessels from each other.

3. An apparatus as claimed in claim 1 further comprising means for feeding reaction vessels which are in the form of a strip made of a light transmitting synthetic resin having excellent chemical resistance and in which strip reaction vessels are arranged in a row along the strip and with slots along the opposite sides of the row, said feeding means comprising a storage means in which the sheets are stored in a coil, means for feeding the strip out of said storage means, means for cutting the strip being fed for separating individual reaction vessels from the strip one by one and placing them on said reaction vessel transfer device.

4. An apparatus as claimed in claim 1 in which said reagent discharging device includes reagent containing vessels for containing reagent to be dispensed, and in which control device further comprises means for optically measuring the volume of reagent contained in each reagent containing vessel and determines the number of amounts of reagent which can be dispensed from such reagent containing vessel and a display means for displaying the number.

5. An apparatus as claimed in claim 1 in which said stirring device comprises a tube through which the gas is supplied, means for inserting the free end of said tube into a reaction vessel and then withdrawing it, means for cutting off a length of tube which has been inserted into the reaction vessel, and means for feeding the tube in the direction toward its free end for replacing the cut off length.

6. An apparatus for carrying out automatic analysis of a specimen carried in a transparent reaction vessel, said apparatus comprising:
    a transfer path along which reaction vessels are transferred one by one in a linear manner, said path having therealong and in the recited order a specimen discharging position, at least one reagent discharging position, a series of successive optical measuring positions, and a reaction vessel disposal position;
    a reaction vessel transfer device for successively transferring reaction vessels along said transfer path for bringing successive reaction vessels to each position one at a time;
    a specimen discharging device at said specimen discharging position for discharging a predetermined amount of a specimen to be analyzed into a reaction vessel at said specimen discharging position;
    at least one reagent discharging device at said at least one reagent discharge position for discharging a predetermined amount of a reagent at said reagent discharging position;
    a stirring device along said transfer path between said at least one reagent discharge position and the first of said series of optical measuring positions for supplying gas for stirring the liquid in each reaction vessel;
    an optical measuring device for passing a beam of light through the liquid in each reaction vessel, said optical measuring device including a light source and a photoelectric element disposed on opposite sides of said transfer path in face-to-face opposed relation to each other, and a filtering device in the path of the light beam from said light source for permitting the passage of light having a specific wavelength corresponding to the specimen being analyzed, said optical measuring device being movable along said transfer path past said succession of optical measuring positions in the direction of movement of each reaction vessel along said transfer path for directing the beam of light through each reaction vessel at said optical measuring positions;
    an optical measuring device transfer means connected to said optical measuring device for moving said optical measuring device along said transfer path;
    said reagent discharging device including reagent containing vessels for containing reagent to be dispensed;
    a control device connected to said optical measuring device and comprising means for analyzing the data obtained by said optical measuring device and means for optically measuring the volume of reagent contained in each reagent containing vessel and determining the number of amounts of reagent which can be dispensed from such reagent containing vessel and a display means for displaying the number, and
    a disposal device at said reaction vessel disposal position for discarding, without cleaning, each reaction vessel the optical measurements of which are finished.

7. An apparatus for carrying out automatic analysis of a specimen carried in a transparent reaction vessel, said apparatus comprising:
    a transfer path along which reaction vessels are transferred one by one in a linear manner, said path having therealong and in the recited order a specimen discharging position, at least one reagent discharging position, a series of successive optical measuring positions, and a reaction vessel disposal position;
    a reaction vessel transfer device for successively transferring reaction vessels along said transfer path for bringing successive reaction vessels to each position one at a time;
    a specimen discharging device at said specimen discharging position for discharging a predetermined amount of a specimen to be analyzed into a reaction vessel at said specimen discharging position;
    at least one reagent discharging device at said at least one reagent discharge position for discharging a predetermined amount of a reagent at said reagent discharging position;
    a stirring device along said transfer path between said at least one reagent discharge position and the first of said series of optical measuring positions for supplying gas for stirring the liquid in each reaction vessel, said stirring device having a tube through which the gas is supplied, means for inserting the free end of said tube into a reaction vessel and then withdrawing it, means for cutting off the length of tube which has been inserted into a reaction vessel, and means for feeding the tube in the direction toward its free end for replacing the cut off length;
    an optical measuring device for passing a beam of light through the liquid in each reaction vessel, said optical measuring device including a light source and a photoelectric element disposed on opposite sides of said transfer path in face-to-face opposed relation to each other, and a filtering device in the path of the light beam from said light source for permitting the passage of light having a specific wavelength corresponding to the specimen being analyzed, said optical measuring device being movable along said transfer path past said succession of optical measuring positions in the direction of movement of each reaction vessel along said transfer path for directing the beam of light through each reaction vessel at said optical measuring positions;
    an optical measuring device transfer means connected to said optical measuring device for moving said optical measuring device along said transfer path;
    a control device connected to said optical measuring device and comprising means for analyzing the data obtained by said optical measuring device; and
    a disposal device at said reaction vessel disposal position for discarding, without cleaning, each reaction vessel the optical measurements of which are finished.

* * * * *